(12) United States Patent
Kok

(10) Patent No.: US 7,999,943 B2
(45) Date of Patent: *Aug. 16, 2011

(54) DEVICE MANUFACTURING METHOD WITH ANGULAR-RESOLVED SPECTROSCOPIC LITHOGRAPHY CHARACTERIZATION

(75) Inventor: Martinus Joseph Kok, Eindhoven (NL)

(73) Assignee: ASML Netherlands B.V., Veldhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 12/783,961

(22) Filed: May 20, 2010

(65) Prior Publication Data
US 2010/0220308 A1 Sep. 2, 2010

Related U.S. Application Data

(63) Continuation of application No. 11/478,306, filed on Jun. 30, 2006.

(51) Int. Cl.
*G01N 21/55* (2006.01)
(52) U.S. Cl. ........................ 356/445; 356/400
(58) Field of Classification Search .......... 356/399–401, 356/625–635, 445–448
See application file for complete search history.

(56) References Cited

U.S. PATENT DOCUMENTS

| | | |
|---|---|---|
| 5,703,692 A | 12/1997 | McNeil et al. |
| 5,880,838 A | 3/1999 | Marx et al. |
| 5,963,329 A | 10/1999 | Conrad et al. |
| 6,525,803 B2 * | 2/2003 | Kwan et al. ............ 355/53 |
| 6,608,690 B2 | 8/2003 | Niu et al. |
| 6,699,624 B2 | 3/2004 | Niu et al. |
| 6,704,661 B1 | 3/2004 | Opsal et al. |
| 6,721,691 B2 | 4/2004 | Bao et al. |
| 6,738,138 B2 | 5/2004 | Wei |
| 6,753,961 B1 | 6/2004 | Norton et al. |
| 6,768,983 B1 | 7/2004 | Jakatdar et al. |
| 6,772,084 B2 | 8/2004 | Bischoff et al. |
| 6,785,638 B2 | 8/2004 | Niu et al. |
| 6,813,034 B2 | 11/2004 | Rosencwaig et al. |
| 6,819,426 B2 | 11/2004 | Sezginer et al. |
| 6,856,408 B2 | 2/2005 | Raymond |
| 6,919,964 B2 | 7/2005 | Chu |
| 6,928,628 B2 | 8/2005 | Seligson et al. |
| 6,972,852 B2 | 12/2005 | Opsal et al. |
| 6,974,962 B2 | 12/2005 | Brill et al. |

(Continued)

FOREIGN PATENT DOCUMENTS

DE 010038060 A1 * 5/2001

(Continued)

OTHER PUBLICATIONS

Abstract of Japanese Patent Application No. JP2003-0534994 T, published Feb. 24, 2005.

(Continued)

*Primary Examiner* — Hoa Q Pham
(74) *Attorney, Agent, or Firm* — Sterne, Kessler, Goldstein & Fox P.L.L.C.

(57) ABSTRACT

To inspect all portions of the substrate, the substrate table can be moved rotationally and linearly. Furthermore, the detector can be moved rotationally. This allows all portions of a surface of the substrate to be inspected from all angles in a plane parallel to the substrate. In one example, as less linear motion is needed, the apparatus occupies a smaller volume and generates smaller vibrations.

8 Claims, 5 Drawing Sheets

U.S. PATENT DOCUMENTS

| | | | |
|---|---|---|---|
| 6,987,572 B2 | 1/2006 | Lakkapragada et al. | |
| 7,046,376 B2 | 5/2006 | Sezginer | |
| 7,053,991 B2* | 5/2006 | Sandusky | 355/77 |
| 7,061,615 B1 | 6/2006 | Lowe-Webb | |
| 7,061,623 B2 | 6/2006 | Davidson | |
| 7,061,627 B2 | 6/2006 | Opsal et al. | |
| 7,068,363 B2 | 6/2006 | Bevis et al. | |
| 7,110,099 B2 | 9/2006 | Littau et al. | |
| 7,215,431 B2 | 5/2007 | Opsal | |
| 7,224,432 B2 | 5/2007 | Sasaki et al. | |
| 7,336,012 B2 | 2/2008 | Tanaka | |
| 7,659,988 B2* | 2/2010 | Kok et al. | 356/445 |
| 2003/0032085 A1 | 2/2003 | Scott et al. | |
| 2004/0105099 A1* | 6/2004 | Nikoonahad | 356/601 |
| 2004/0119970 A1 | 6/2004 | Dusa et al. | |
| 2004/0257571 A1* | 12/2004 | Mieher et al. | 356/401 |
| 2006/0033921 A1 | 2/2006 | Den Boef et al. | |
| 2006/0066855 A1 | 3/2006 | Den Boef et al. | |
| 2006/0076509 A1* | 4/2006 | Okino et al. | 250/492.2 |
| 2006/0126074 A1 | 6/2006 | Van Der Werf et al. | |
| 2006/0139592 A1 | 6/2006 | Den Boef et al. | |
| 2006/0187428 A1* | 8/2006 | Bleeker et al. | 355/53 |
| 2007/0279644 A1 | 12/2007 | Teun Plug et al. | |
| 2008/0002207 A1 | 1/2008 | Kok et al. | |
| 2008/0266560 A1 | 10/2008 | Kok | |

FOREIGN PATENT DOCUMENTS

| | | |
|---|---|---|
| JP | 2004-048869 A | 2/2004 |
| JP | 2004-349285 A | 12/2004 |
| JP | 2005-354022 A | 12/2005 |
| WO | WO 03/032085 A3 | 4/2003 |
| WO | WO 2004/105105 | 12/2004 |

OTHER PUBLICATIONS

Non-Final Rejection mailed Sep. 8, 2008 for U.S. Appl. No. 11/478,306, 6 pgs.

Final Rejection mailed Mar. 9, 2009 for U.S. Appl. No. 11/478,306, 7 pgs.

Non-Final Rejection mailed Jul. 17, 2009 for U.S. Appl. No. 11/478,306, 9 pgs.

Final Rejection mailed Dec. 14, 2009 for U.S. Appl. No. 11/478,306, 10 pgs.

Notice of Allowance mailed Apr. 26, 2010 for U.S. Appl. No. 11/478,306, 6 pgs.

Non-Final Rejection mailed Oct. 29, 2008 for U.S. Appl. No. 11/704,375, 11 pgs.

Notice of Allowance mailed Sep. 17, 2009 for U.S. Appl. No. 11/704,375, 6pgs.

Notice of Reasons for Rejection for Japanese Patent Application No. JP20070164954, drafted Jun. 25, 2010.

English-Language Translation of Decision of Rejection directed to Japanese Patent Application No. 2004-164954, mailed on Jan. 24, 2011, from the Japanese Patent Office; 2 pages.

English language Abstract for JP 2004-048869 A, published Feb. 12, 2004; 1 page.

Non-Final Rejection mailed Aug. 26, 2010 directed to U.S. Appl. No. 11/478,306, filed Jun. 30, 2006; 7 pages.

Notice of Allowance mailed Jan. 27, 2011 directed to U.S. Appl. No. 11/478,306, filed Jun. 30, 2006; 6 pages.

* cited by examiner

Intensity wavelength

DEVICE MANUFACTURING METHOD WITH ANGULAR-RESOLVED SPECTROSCOPIC LITHOGRAPHY CHARACTERIZATION

CROSS REFERENCE TO RELATED APPLICATIONS

This application is a continuation of U.S. application Ser. No. 11/478,306, filed Jun. 30, 2006, now allowed, which is incorporated by reference in its entirety.

This application is related to U.S. application Ser. No. 11/704,375, filed Feb. 9, 2007 (now U.S. Pat. No. 7,659,988), which is incorporated by reference herein in its entirety.

BACKGROUND OF THE INVENTION

1. Field of the Invention

The present invention relates to an apparatus used for inspection, for example, in the manufacture devices by lithographic techniques and a device manufacturing method.

2. Description of the Related Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on a individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include steppers, in which each target portion is irradiated by exposing an entire pattern onto the target portion at one time, and scanners, in which each target portion is irradiated by scanning the pattern through a radiation beam in a given direction (the "scanning" direction) while synchronously scanning the substrate parallel or anti-parallel to this direction. It is also possible to transfer the pattern from the patterning device to the substrate by imprinting the pattern onto the substrate.

In order to determine features of the substrate, such as its alignment, a beam is reflected off the surface of the substrate, for example at an alignment target, and an image is created on a camera of the reflected beam. By comparing the properties of the beam before and after it has been reflected off the substrate, the properties of the substrate can be determined. This can be done, for example, by comparing the reflected beam with data stored in a library of known measurements associated with known substrate properties.

To inspect different points on the substrate the substrate must be moved relative to the detector. To inspect every point on the substrate the detector and substrate must be moveable with respect to each other in two directions. Furthermore, due to possible rotational asymmetry in the apparatus, it must be possible to detect every point on the substrate from every rotational angle to the substrate (i.e., the detector and substrate must be configured to detect any point on the substrate at any given rotation with respect to each other).

Conventionally, the substrate table has been moveable in a first linear direction and rotationally, and the detector has been moveable in a second linear direction (perpendicularly to the first linear direction). However, such linear movement requires a lot of space (the substrate table and detector must both be moved by at least 300 mm) and furthermore generates large acceleration forces resulting in significant vibrations.

It is desirable to provide scatterometry apparatus near and amongst the lithographic apparatus in a clean environment. Space in such environments is at a premium and therefore it is desirable to minimize the space occupied by the apparatus.

As is well known, accuracy of exposure in the lithographic apparatus is very important and because the scatterometry apparatus are often arranged near the lithographic apparatus, it is desirable to minimize the vibrations resulting from the use of the scatterometry apparatus.

SUMMARY OF THE INVENTION

Accordingly, it is desirable to provide a device manufacturing method comprising projecting a patterned beam of radiation onto a substrate; moving the substrate linearly to be at the focal point of a detector; rotating the substrate about an axis perpendicular to the plane of the substrate; rotating the detector; and detecting an angle resolved spectrum reflected from the substrate. According to a further embodiment of the invention there is provided a device manufacturing method comprising projecting a patterned beam of radiation onto a surface of a substrate; moving the substrate linearly to be at the focal point of a detector; rotating the detector, using a rotor, about an axis perpendicular to the surface; and detecting an angle resolved spectrum reflected from the substrate.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
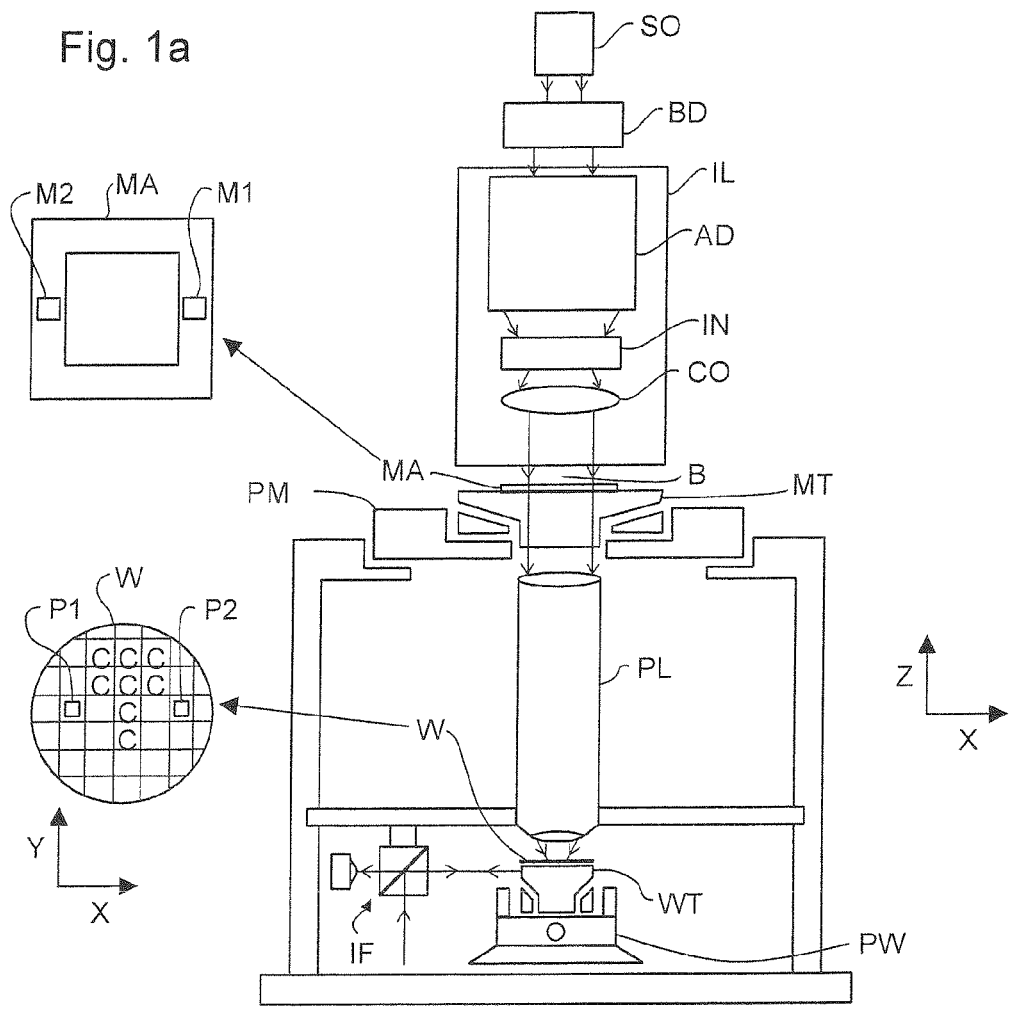
FIG. 1a depicts a lithographic apparatus according to an embodiment of the invention.

FIG. 1a schematically depicts a lithographic apparatus. The apparatus comprises an illumination system (illuminator) IL configured to condition a radiation beam B (e.g., UV radiation or EUV radiation). A support (e.g., a mask table) MT is configured to support a patterning device (e.g., a mask) MA and is connected to a first positioner PM configured to accurately position the patterning device in accordance with certain parameters. A substrate table (e.g., a wafer table) WT is configured to hold a substrate (e.g., a resist-coated wafer) W and connected to a second positioner PW configured to accurately position the substrate in accordance with certain parameters. A projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, to direct, shape, and/or control radiation.

The support supports, e.g., bears the weight of, the patterning device. It holds the patterning device in a manner that depends on the orientation of the patterning device, the design of the lithographic apparatus, and other conditions, such as for example whether or not the patterning device is held in a vacuum environment. The support can use mechanical, vacuum, electrostatic, or other clamping techniques to hold the patterning device. The support may be a frame or a table, for example, which may be fixed or moveable as required. The support may ensure that the patterning device is at a desired position, for example, with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section as to create a pattern in a target portion of the substrate. It should be noted that the pattern imparted to the radiation beam may not exactly correspond to the desired pattern in the target portion of the substrate, for example, if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small minors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic, and electrostatic optical systems, or any combination thereof, as appropriate for the exposure of radiation being used, or for other factors such as the use of an immersion liquid or the use of a vacuum. Any use of the term "projection lens" herein may be considered as synonymous with the more general term "projection system."

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives radiation from a radiation source SO. The source and the lithographic apparatus may be separate entities, for example, when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases, the source may be an integral part of the lithographic apparatus, for example, when the source is a mercury lamp. The source SO and the illuminator IL, together with the beam delivery system BD if required, may be referred to as a radiation system.

The illuminator IL may comprise an adjuster AD to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, or capacitive sensor), the substrate table WT can be moved accurately, e.g., so as to position different target portions C in the path of the radiation B beam. Similarly, the first positioner PM and another position sensor (which is not explicitly depicted in FIG. 1a) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are know as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
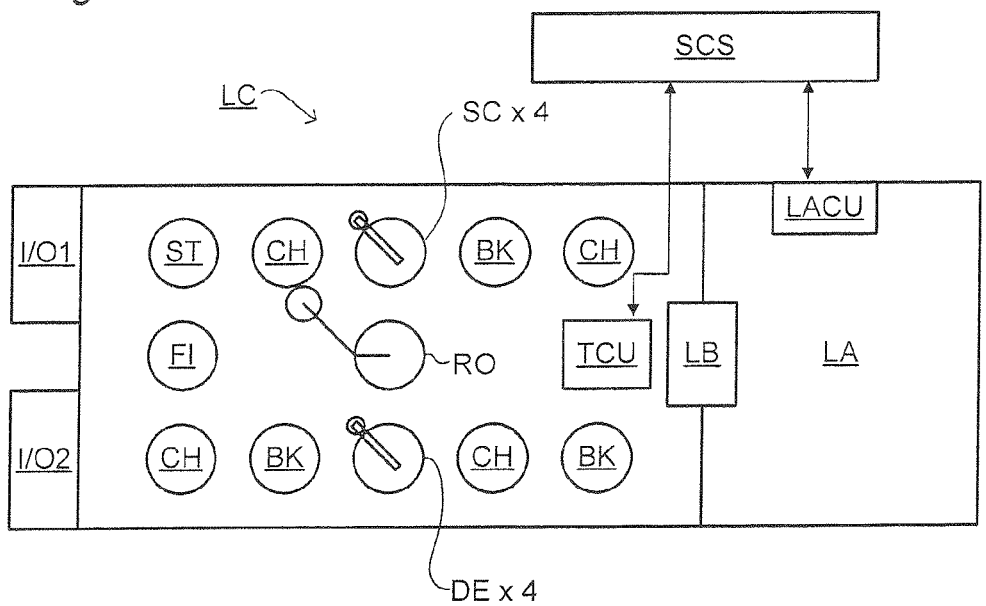
FIG. 1b depicts a lithographic cell or cluster according to an embodiment of the invention.

As shown in FIG. 1b, the lithographic apparatus LA forms part of a lithographic cell LC, also sometimes referred to a lithocell (lithographic cell) or cluster, which also includes apparatus to perform pre- and post-exposure processes on a substrate. Conventionally, these include spin coaters SC to deposit resist layers, developers DE to develop exposed resist, chill plates CH, and bake plates BK. A substrate handler, or robot, RO picks up substrates from input/output ports I/O1, I/O2, moves them between the different process apparatus and delivers them to the loading bay LB of the lithographic apparatus. These devices, which are often collectively referred to as the track, are under control of a track control unit TCU which is itself controlled by the supervisory control system SCS, which also controls the lithographic apparatus. Thus, the different apparatus can be operated to maximize throughput and processing efficiency.

In order that the substrates that are exposed by the lithographic apparatus are exposed consistently for each layer of resist, there are certain properties of the substrate that should be measured to determine whether there are changes in alignment, rotation, etc., that must be compensated for by the lithographic apparatus. A separate inspection apparatus is used to determine the properties of the substrates, and in particular, how the properties of different substrates or different layers of the same substrate vary from layer to layer.

Figure 2:
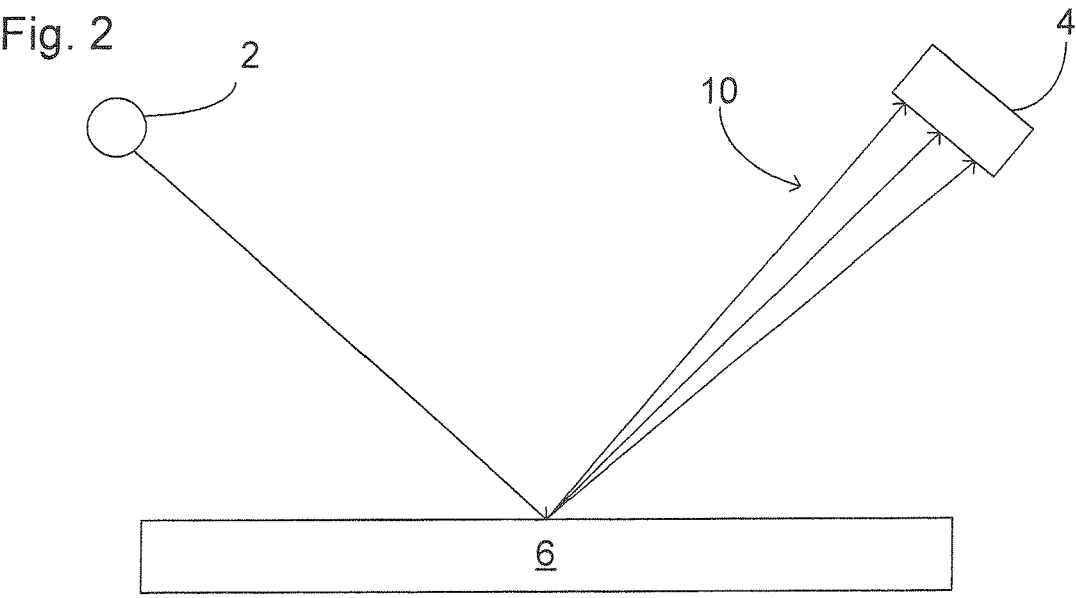
FIG. 2 depicts a scatterometer that may be used as a sensor in the present invention.
Figure 2:
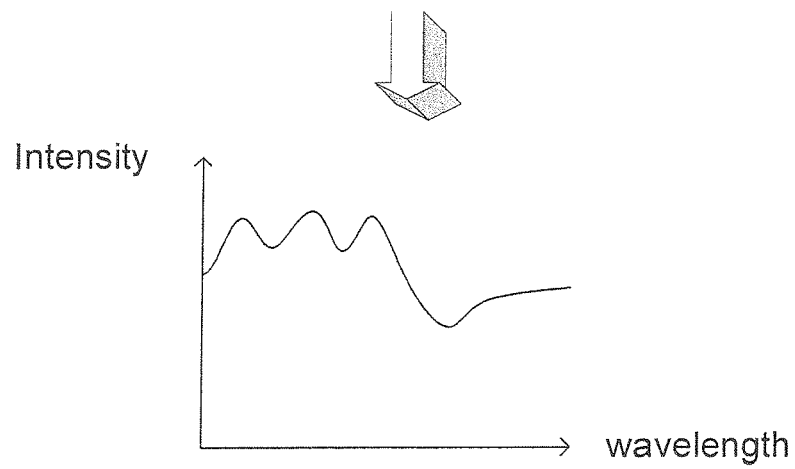
Figure 2:
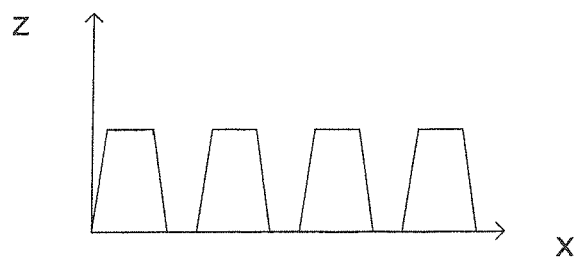

The properties of the surface of a substrate W may be determined using a sensor such as a scatterometer such as that depicted in FIG. 2. The scatterometer comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconfigured, e.g., by Rigorous Coupled Wave Analysis and non-linear regression, or by comparison with a library simulated spectra as shown at the bottom of FIG. 2. In general, for the reconstruction the general form of the structure is known and some parameters are assumed from knowledge of the process by which the structure was made, leaving only a few parameters of the structure to be determined from the scatterometry data.

The scatterometer may be normal-incidence scatterometer or an oblique-incidence scatterometer. Variants of scatterometry may also be used in which the reflection is measured at a range of angles of a single wavelength, rather than the reflection at a single angle of a range of wavelengths.

Figure 3:
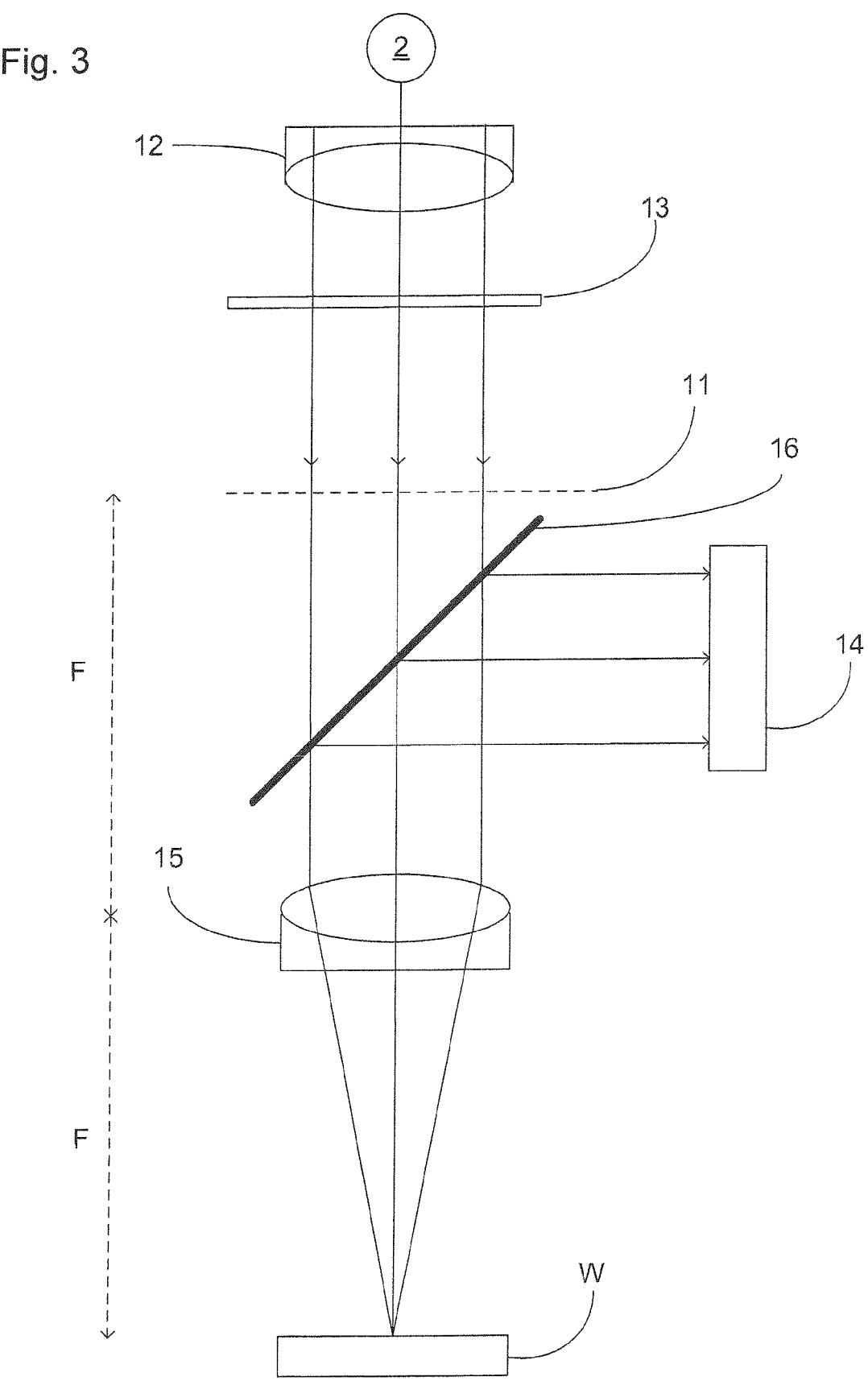
FIG. 3 depicts the general operating principle of measuring an angle resolved spectrum in the pupil plane of a high NA lens.

Scatterometers for measuring properties of a substrate may measure, in the pupil plane 11 of a high numerical aperture lens, the properties of an angle-resolved spectrum reflected from the substrate surface W at a plurality of angles and wavelengths as shown in FIG. 3. Such a scatterometer may comprise a radiation projector 2 for projecting radiation onto the substrate and a detector 14 for detecting the reflected spectra. The pupil plane is the plane in which the radial position of radiation defines the angle of incidence and the angular position defines azimuth angle of the radiation. The detector 14 is placed in the pupil plane of the high numerical aperture lens. The numerical aperture may be high and desirably at least 0.9 and more desirably at least 0.95. Immersion scatterometers may even have lenses with numerical apertures over 1.

Some angle-resolved scatterometers only measure the intensity of scattered light. However, more recent scatterometers allow several wavelengths to be measured simultaneously at a range of angles. The properties measured by the scatterometer for different wavelengths and angles may be the intensity of transverse magnetic- and transverse electric-polarized light and the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of, say, $\delta\gamma$ and a spacing, therefore, of at least $2\delta\gamma$ (i.e., twice the bandwidth). Several "sources" of radiation can be different portions of an extended radiation source which have been split using, say, fiber bundles. In this way, angle resolved scatter spectra can be measured at multiple wavelengths in parallel. A 3-D spectrum (wavelength and two different angles) is measured, which contains more information than a 2-D spectrum. This allows more information to be measured which increases metrology process robustness.

A scatterometer that may be used with the present invention is shown in FIG. 3. The radiation of the radiation projector 2 is focused using lens system 12 through interference filter 13 and is focused onto substrate W via a microscope objective lens 15. The radiation is then reflected via partially reflective surface 16 into a CCD detector 14 in the back projected pupil plane 11 in order to have the scatter spectrum detected. The pupil plane 11 is at the focal length of the lens system 15. A detector and high aperture lens are placed at the pupil plane. The pupil plane may be re-imaged with auxiliary optics since the pupil plane of a high-NA lens is usually located inside the lens.

The pupil plane of the reflected radiation is imaged on the CCD detector with an integration time of, for example, 40 milliseconds per frame. In this way, a two-dimensional angular scatter spectrum of the substrate targets is imaged on the detector. The detector may be, for example, an array of CCD detectors or CMOS detectors.

A set of interference filters 13 is available to select a wavelength of interest in the range of, say 405-790 nm or even lower, such as 200-300 nm. The interference filter may be tunable rather than comprising a set of different filters. A grating could be used instead of interference filters.

The substrate W or even the partially reflective surface 16 may be grating. The grating may be printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process from knowledge of the printing step and/or other scatterometry processes.

Figure 4:
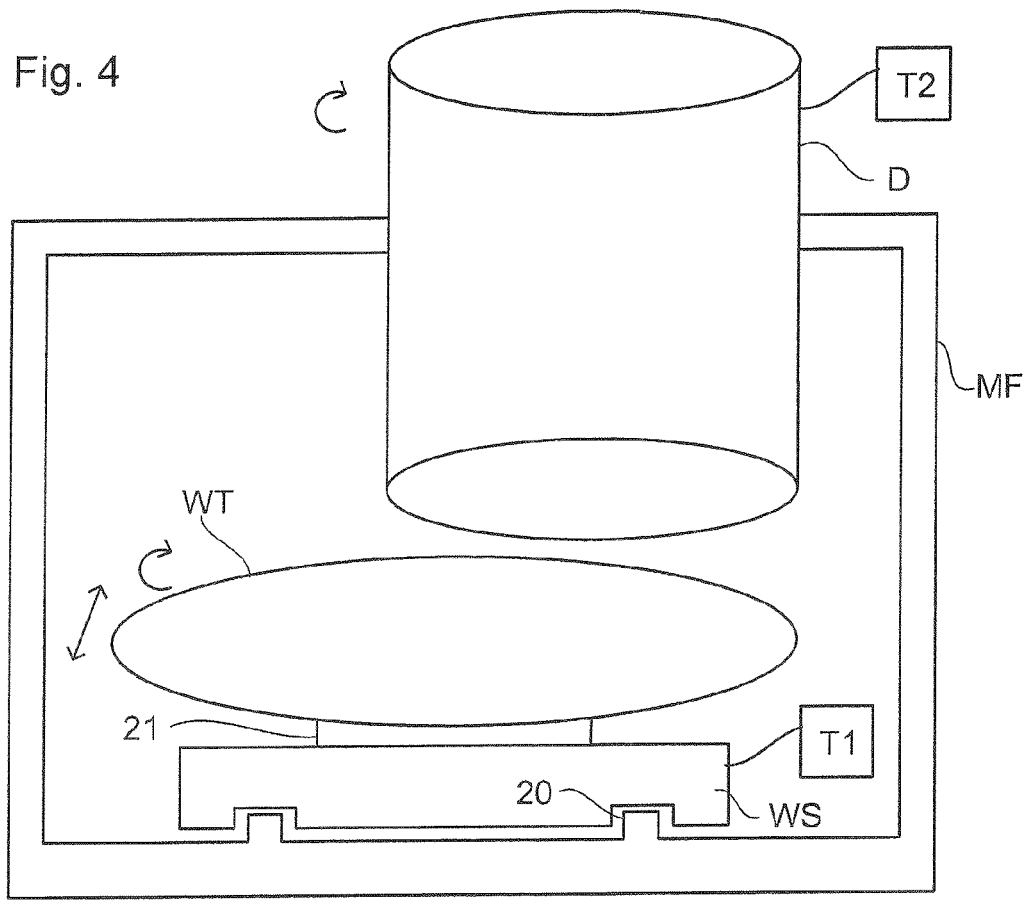
FIG. 4 depicts an arrangement according to a first embodiment of the invention.

It may be desirable to inspect different portions of the surface of the substrate W. As such, the substrate W and the detector 14 are moved relative to each other and FIG. 4 depicts an apparatus according to an embodiment of the invention for achieving this. The substrate table WT holding the substrate W is arranged on a substrate stage WS which can be moved linearly along tracks 20 using motor T1. The tracks 20 may be arranged on mount frame MF, on which the detector D is mounted or alternatively on a separate frame (not depicted). Additionally, the substrate table WT can be rotated, using a rotor portion 21, relative to the substrate stage. Linear and rotational movement of the substrate table WT enables radiation reflected from every part of the substrate to be detected and every portion of the substrate examined. However, it is also desirable to be able to view every portion of the surface of the substrate from every angle so in addition to the detecting portion D can also be rotated, using a rotor T2, about an axis perpendicular to the plane of the substrate. Thus, every part of the surface of the substrate can be viewed from every angle in a plane parallel to the plane of the substrate.

Desirably, rotation of an object generally causes less severe vibrations and requires a smaller volume than linear motion of an object. Thus, by enabling all portions of the substrate to be inspected by rotation of both the detector and the substrate table and just using linear motion of the substrate table (rather than using linear motion of both the substrate table and the detector or two dimensional linear motion of the detector, as is conventional) fewer and smaller vibrations and disturbances will be caused and the apparatus occupies a smaller volume.

Figure 5:
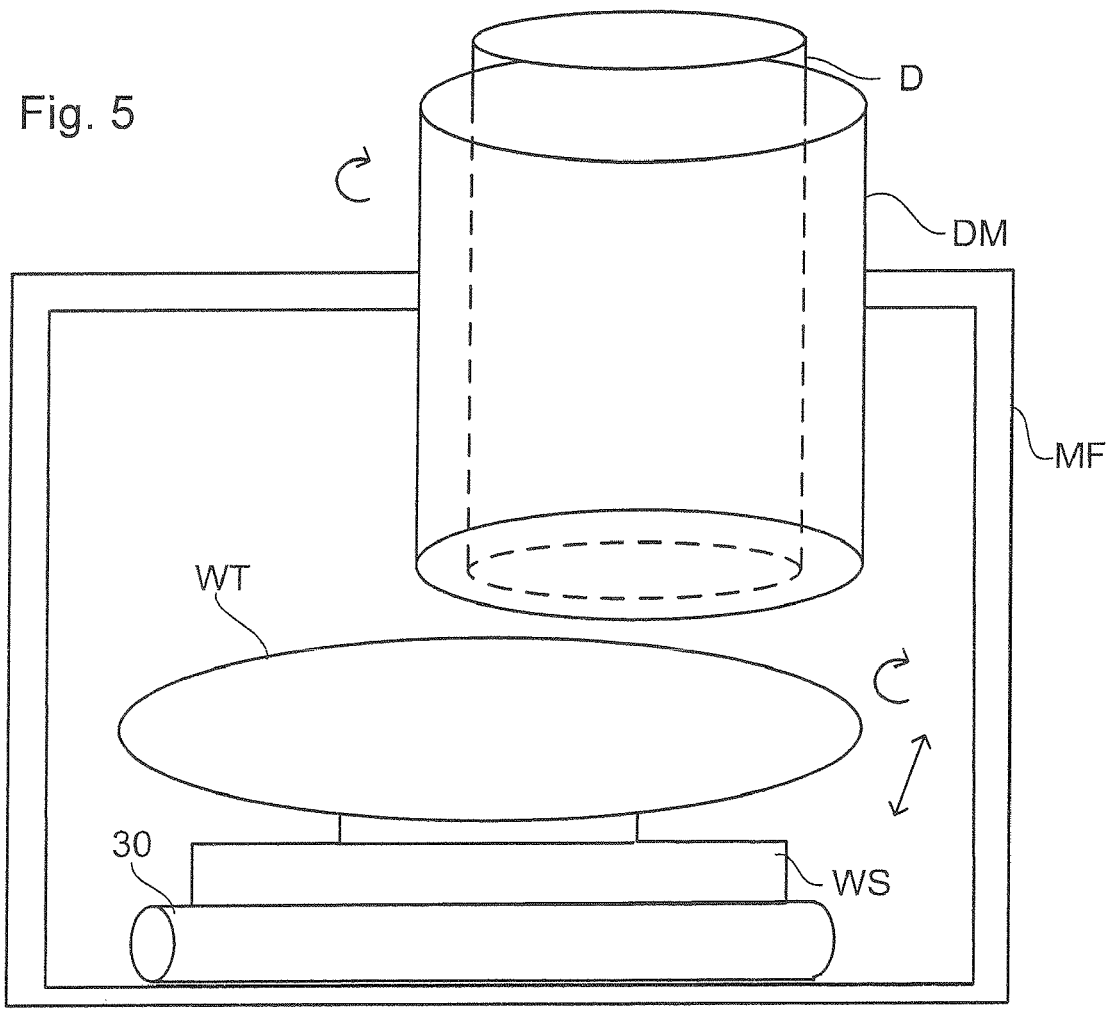
FIG. 5 depicts an arrangement according to a second embodiment of the invention.

Although the apparatus in FIG. 4 shows the substrate stage as being moved along tracks 20, the substrate stage could alternatively be moved along rollers 30, as shown in FIG. 5. Indeed any sort of method of linear transportation would be suitable, but ones which minimize vibrations are desired. To further reduce the vibrations, the substrate stage may be supported on bearings, desirably air bearings.

Also depicted in FIG. 5, the detector D may be mounted on a detector mount DM. A rotor then rotates the detector relative to the detector mount. The detector and/or the detector mount are preferably supported on bearings, desirably air bearings.

After the substrate stage has been moved and the substrate table and detecting portion D rotated, the positions and orientations of the detecting portion D and substrate table may be measured prior to detecting the, for example, grating.

Although described here in conjunction with a lithographic apparatus such an arrangement may be used in conjunction with other types of scatterometer.

The descriptions above are intended to be illustrative, not limiting. Thus, it will be apparent to one skilled in the art that modifications may be made to the invention as described without departing from the scope of the claims set out below.

What is claimed is:

1. A device manufacturing method, comprising:
    projecting a patterned beam of radiation onto a surface of a substrate;
    moving the substrate linearly along a first axis to a focal point of a detector;
    rotating the detector, using a rotor, about a second axis perpendicular to the surface and perpendicular to the first axis;
    rotating the substrate about the second axis; and
    detecting an angle resolved spectrum reflected from the substrate.

2. The device manufacturing method of claim 1, further comprising:
    moving the substrate linearly along a third axis parallel to the surface of the substrate and perpendicular to the first axis.

3. The device manufacturing method of claim 1, wherein the substrate is held on a substrate table.

4. The device manufacturing method of claim 3, wherein the substrate table is supported by bearings.

5. The device manufacturing method of claim 4, wherein the bearings comprise air bearings.

6. The device manufacturing method of claim 1, wherein the detector is mounted on a mount and the rotor rotates the detector relative to the mount.

7. The device manufacturing method of claim 6, wherein the detector is supported by bearings.

8. The device manufacturing method of claim 7, wherein the bearings comprise air bearings.

* * * * *